(12) United States Patent
Dyer et al.

(10) Patent No.: US 6,239,165 B1
(45) Date of Patent: May 29, 2001

(54) LIQUID PHARMACEUTICAL FORMULATION CONTAINING ZOTEPINE

(75) Inventors: Ann Margaret Dyer; Alan Smith, both of Nottingham (GB)

(73) Assignee: Knoll Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/600,980

(22) PCT Filed: Jan. 27, 1999

(86) PCT No.: PCT/EP99/00533

§ 371 Date: Jul. 25, 2000

§ 102(e) Date: Jul. 25, 2000

(87) PCT Pub. No.: WO99/39709

PCT Pub. Date: Aug. 12, 1999

(30) Foreign Application Priority Data

Feb. 7, 1998 (GB) .................................................. 9802617

(51) Int. Cl.[7] ...................................................... A61K 31/38

(52) U.S. Cl. ................................................................ 514/431
(58) Field of Search ............................................... 514/431

(56) References Cited

U.S. PATENT DOCUMENTS 4,443,469   4/1984   Nishizono ............................ 424/275

FOREIGN PATENT DOCUMENTS

| 733 368 A1 | 9/1996 | (EP) . |
| 1 247 067 | 9/1971 | (GB) . |
| WO 97/23477 | 7/1997 | (WO) . |

*Primary Examiner*—James H. Reamer
(74) *Attorney, Agent, or Firm*—Keil & Weinkauf

(57) ABSTRACT

A liquid pharmaceutical formulation comprising a) 2 to 7% w/v of Zotepine; b) 0.5 to 35% w/v of an organic acid selected from the group consisting of ascorbic acid, citric acid, fumaric acid, glutaric acid, lactic acid, malic acid, sorbic acid and tartaric acid; c) 15 to 60% v/v of ethanol and d) a liquid diluent to 100%; which may be used as drops or in a drink.

23 Claims, No Drawings

LIQUID PHARMACEUTICAL FORMULATION CONTAINING ZOTEPINE

This invention relates to a liquid pharmaceutical formulation containing Zotepine.

Zotepine is 2-[(8-chlorodibenzo[b,f]thiepin-10-yl)oxy]-N,N-dimethylethylamine as shown in formula I.

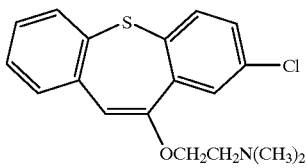

The preparation and the psychotropic and neurotropic activity of Zotepine are described in British Patent Specification 1247067 (Fujisawa). The use of Zotepine in the treatment of gout is described in U.S. Pat. No. 4,443,469 (Fujisawa). The use of Zotepine for preventing relapse in chronic schizophrenic patients is described in British patent application 9526264.8 (Knoll AG). 2-[(8-Chlorodibenzo[b,f]-thiepin-10-yl)oxy]-N,N-dimethylethylamine has been available on prescription for the treatment of schizophrenia in Japan since 1982 under the tradename "Lodopin®", and in Germany since 1990 under the tradename "Nipolept®". Zotepine is also known under the tradename "Zoleptil®".

Zotepine is currently only available in tablet form. However, patient compliance is a well-known problem with anti-psychotic drugs. It would be advantageous to provide Zotepine in a liquid formulation which might be added as drops to food or administered in a drink. However, Zotepine has a low solubility in solvents which would commonly be used in the pharmaceutical industry to prepare oral liquid formulations.

Solubility of Zotepine may be improved by converting it into an acid addition salt, but solutions of acid addition salts are unstable on storage due to acid hydrolysis which produces 8-chlorodibenzo[b,f]thiepine-10(11H)-one. In addition Zotepine in solution may undergo oxidation to give the N-oxide over time. Surprisingly a formulation has now been found which provides Zotepine in a liquid formulation which is stable to storage.

Accordingly, the present invention provides a liquid pharmaceutical formulation comprising
a) 2 to 7% w/v of Zotepine
b) 0.5 to 35% w/v of an organic acid selected from the group consisting of ascorbic acid, citric acid, fumaric acid, glutaric acid, lactic acid, malic acid, sorbic acid and tartaric acid
c) 15 to 60% v/v of ethanol and
d) a liquid diluent to 100%.

Preferably the organic acid is selected from the group consisting of citric acid, malic acid and lactic acid, more preferably the organic acid is lactic acid.

Preferably the liquid diluent is water, polyethylene glycol or sesame oil or mixtures thereof. More preferably the diluent is water or polyethylene glycol. Most preferably the diluent is polyethylene glycol.

In a preferred embodiment the present invention provides a liquid pharmaceutical formulation comprising
a) 4 to 6% w/v of Zotepine
b) 2 to 15% w/v of an organic acid selected from the group consisting of ascorbic acid, citric acid, fumaric acid, glutaric acid, lactic acid, malic acid, sorbic acid and tartaric acid
c) 20 to 30% v/v of ethanol and
d) polyethylene glycol to 100%.

Preferably the organic acid is selected from the group consisting of citric acid, malic acid and lactic acid, more preferably the organic acid is lactic acid.

Preferably the amount of organic acid used is in the range of 3 to 7% w/v of the formulation. Most preferably the amount of organic acid used is in the range of 4 to 6% w/v of the formulation.

The above formulations overcome the problems of the low solubility of Zotepine combined with the instability of the Zotepine in acidic solution. The formulations also overcome the poor taste characteristics of Zotepine and allow ease of dispersion into water. The above formulations have good shelf-lives and are well preserved.

Preferably the formulation comprises 22 to 28% v/v of ethanol. More preferably the formulation comprises 24–26% v/v of ethanol.

In a second preferred embodiment the present invention provides a liquid pharmaceutical formulation comprising
a) 4 to 6% w/v of Zotepine
b) 15 to 35% w/v of an organic acid selected from the group consisting of ascorbic acid, citric acid, fumaric acid, glutaric acid, lactic acid, malic acid, sorbic acid and tartaric acid
c) 20 to 50% v/v of ethanol and
d) water to 100%.

Preferably the organic acid is selected from the group consisting of citric acid, malic acid and lactic acid, more preferably the organic acid is lactic acid.

Preferably the amount of organic acid used is in the range of 18 to 32% w/v of the formulation. Most preferably the amount of organic acid used is in the range of 20 to 30% w/v of the formulation.

When the diluent is water the amount of organic acid used is selected such that the pH of the final formulation lies in the range of 2.2 to 2.6.

Optionally the pharmaceutical liquid formulation contains a preservative. Preferably the preservative is benzyl alcohol (which can further enhance the solubility of Zotepine by acting as a solubilizer) or an anti-oxidant or an anti-oxidant synergist or mixtures thereof. The preparation may also include an antioxidant, or antioxidant synergists, to prevent oxidative degradation. Any of the known antioxidants may be used, for example alpha tocopherol, ascorbic acid, ascorbyl palmitate, butylated hydroxyanisole, butylated hydroxytoluene, fumaric acid, malic acid, propyl gallate, sodium ascorbate or sodium metabisulphite or their synergists for example disodium edetate. More preferably the antioxidant is sodium metabisulphite. The level of antioxidant used will be optimised for each formulation, for example for sodium metabisulphite is in the range 0.01 to 1.0% w/v, more preferably in the range 0.075 to 0.2% w/v. The anti-oxidant prevents the formation of Zotepine N-oxide.

A particularly preferred formulation of the present invention comprises
a) 2 to 7% w/v of Zotepine
b) 2 to 15% w/v of an organic acid selected from the group consisting of ascorbic acid, citric acid, fumaric acid, glutaric acid, lactic acid, malic acid, sorbic acid, tartaric acid
c) 20 to 30% w/v of ethanol
d) 0.01 to 1.0% w/v of an anti-oxidant and
e) polyethylene glycol to 100%.

Preferably the formulation comprises 4 to 6% w/v of zotepine.

Preferably the organic acid is selected from the group consisting of citric acid, malic acid and lactic acid, more preferably the organic acid is lactic acid.

Preferably the amount of organic acid used is in the range of 3 to 7% w/v of the formulation. Most preferably the amount of organic acid used is in the range of 4 to 6% w/v of the formulation.

Preferably the anti-oxidant is sodium metabisulphite.

Optionally the liquid pharmaceutical formulation contains one or more flavouring agents. Preferably the flavouring agent is a fruit flavour for example lemon, lime, apple and/or a sweetening agent for example aspartame.

Preferably the flavouring agent is present in an amount of from 0.1% to 5% w/v, more preferably from 0.5% to 1.5% w/v of the formulation.

Optionally the liquid pharmaceutical formulation contains a surfactant which is pharmaceutically acceptable. Preferably the surfactant is a hydrophilic non-ionic surfactant. More preferably the surfactant is polysorbate 80 for example Tween® 80.

Preferably the surfactant is present in an amount of from 0.1% to 2% w/v, more preferably from 0.2 to 1% w/v of the formulation.

The above liquid pharmaceutical formulations are stable on storage and provide commercial products. Preferably the formulation shows a reduction of Zotepine content of less than 10% of the original Zotepine content by weight on storage at ambient temperature for 2 years. More preferably the formulation shows a reduction of Zotepine content of less than 5% on storage at ambient temperature for 2 years. It will be appreciated by those skilled in the art that corresponding reductions in Zotepine content under accelerated storage conditions may also be used to predict the shelf life of the product by extrapolating stability data from accelerated studies to ambient conditions.

The formulations of the present invention are suitable for use as drops. Therefore a further aspect of the present invention provides the formulations described herein in conjunction with a means for delivering drops. Suitable means for delivering drops include a bottle with a cap in the form of a dropper as known to those skilled in the art.

The formulations of the present invention are suitable for use in a metered dosage delivery system such as a pump-action spray or a pressurised aerosol can, in which the propellant is preferably free of oxygen.

Therefore a further aspect of the invention provides a metered dosage delivery system which comprises a liquid formulation as described herein.

Alternatively the formulations may be administered in a drink.

The formulations of the present invention are surprisingly bioequivalent to tablet formulations. Formulations may be prepared according to the present invention which are bioequivalent to 25 mg, 50 mg and 100 mg tablets. Bioequivalence may be demonstrated in humans by methods known to those skilled in the art.

The formulations of the present invention may be used in any known therapeutic uses of Zotepine. In particular, the formulations of the present invention be used in the treatment of schizophrenia, gout, schizoaffective disorders and for preventing relapse in chronic schizophrenic patients.

The invention will now be illustrated by the following non-limiting examples.

EXAMPLE 1

|   | % w/v |
| --- | --- |
| 1 Zotepine | 5.0 |
| 2 Citric acid monohydrate | 30.0 |
| 3 Ethanol 96% | 42.0% v/v |
| 4 Lemon Flavour | 1.5 |
| 4 Lime Flavour | 0.5 |
| 5 Aspartame | 1.0 |
| 6 Purified water to | 100.0 |

*This product contains the equivalent of 40% v/v Absolute Alcohol.

The above example was prepared by mixing ingredients 1, 2, 4 and 5 in a vessel. Ingredient 3 was added with continuous stirring until dissolution was complete. The formulation was made up to volume with ingredient 6 and stirred.

The Zotepine content was assayed by High Performance Liquid Chromatography using constant flow of eluent through a reversed phase silica column in an aqueous/organic mobile phase with acidic pH modifier. The resulting eluents were quantified by electronic integration and visualisation was achieved at an appropriate UV wavelength. The amount of Zotepine remaining, after storage under the conditions given for the time stated, is given in mg/ml. The starting concentration in each example is 50 mg/ml.

The formulations were tested for appearance, zotepine content, pH, density, degradation products and microbiological acceptability at regular intervals.

| Sample Time | 4° C. | 25° C./60% Rh | 30° C./60% Rh |
| --- | --- | --- | --- |
| 2 weeks | 50.2 | 49.4 | 48.9 |
| 1 month | 49.7 | 48.9 | 47.4 |
| 3 months | 49.0 | 46.7 | 46.3 |
| 4 months | 49.8 | 46.9 | 45.0 |
| 6 months | 50.7 | 47.2 | 44.3 |

Rh = Relative humidity

Examples 2 to 6 were prepared and tested in a similar manner to Example 1.

EXAMPLE 2

|   | % w/v (pH 2.4) |
| --- | --- |
| 1 Zotepine | 5.0 |
| 2 Malic acid | 20.0 |
| 3 Ethanol (absolute) | 40.0 v/v |
| 4 Lemon Flavour | 1.5 |
| 4 Lime Flavour | 0.5 |
| 5 Aspartame | 1.0 |
| 6 Purified water to | 100.0 |

| Sample Time | 30° C./60% Rh |
| --- | --- |
| 2 weeks | 51.4 |
| 3 months | 51.6 |
| 6 months | 50.2 |
| 9 months | 51.3 |

EXAMPLE 3

|  | % w/v (pH 2.2) |
|---|---|
| 1 Zotepine | 5.0 |
| 2 Malic acid | 20.0 |
| 3 Ethanol 96%* | 42.0 % v/v |
| 4 Apple Flavour | 0.2 |
| 5 Purified water | to 100.0 |

*This product contains the equivalent of 40% v/v Absolute Alcohol

| Sample Time | 4° C. | 25° C./60% Rh | 30° C./60% Rh | 50° C. |
|---|---|---|---|---|
| 2 weeks | 49.8 | 49.5 | 49.4 | 47.3 |
| 1 month | 50.1 | 49.3 | 49.2 | 49.3 |
| 3 months | 50.1 | 49.1 | 47.2 | — |
| 6 months | 50.1 | 49.0 | 47.5 | — |
| 9 months | 50.5 | 48.5 | 46.3 | — |

EXAMPLE 4

|  | % w/v (pH 2.3) |
|---|---|
| 1 Zotepine | 5.0 |
| 2 Malic acid | 20.0 |
| 3 Ethanol 96%* | 42.0% v/v |
| 4 Lemon Flavour | 1.5 |
| 4 Lime Flavour | 0.5 |
| 5 Purified water | to 100.0 |

*This product contains the equivalent of 40% v/v Absolute Alcohol

| Sample Time | 30° C./60% Rh |
|---|---|
| 2 weeks | 51.4 |
| 3 months | 51.6 |
| 6 months | 50.2 |
| 9 months | 51.3 |

EXAMPLE 5

|  | % w/v (pH 2.3) |
|---|---|
| 1 Zotepine | 5.0 |
| 2 Lactic acid | 30.0 |
| 3 Ethanol 96%* | 31.5% v/v |
| 4 Lemon Flavour | 1.5 |
| 4 Lime Flavour | 0.5 |
| 5 Purified water | to 100.0 |

*This product contains the equivalent of 30% v/v Absolute Alcohol

| Sample Time | 4° C. | 25° C./60% Rh | 30° C./60% Rh | 50° C. |
|---|---|---|---|---|
| 2 weeks | 49.2 | 49.8 | 49.8 | 49.7 |
| 1 month | 51.3 | 51.2 | 50.8 | 49.3 |
| 3 months | 49.2 | 50.1 | 49.8 | — |
| 6 months | 50.0 | 49.8 | 48.8 | — |

EXAMPLE 6

|  | % w/v (pH 2.6) |
|---|---|
| 1 Zotepine | 5.0 |
| 2 Lactic acid | 20.0 |
| 3 Ethanol 96%* | 42.0% v/v |
| 4 Lemon Flavour | 1.5 |
| 4 Lime Flavour | 0.5 |
| 5 Purified water | to 100.0 |

*This product contains the equivalent of 40% v/v Absolute Alcohol

| Sample Time | 30° C./60% Rh | 50° C. |
|---|---|---|
| 1 month | 49.5 | 49.7 |
| 3 months | 50.3 | — |
| 6 months | 50.6 | — |
| 9 months | 51.0 | — |

EXAMPLE 7

|  | % w/v |
|---|---|
| 1 Zotepine | 5.0 |
| 2 Lactic acid | 4.5 |
| 3 Ethanol 96%* | 40.0% v/v |
| 4 Lemon flavour | 1.0% v/v |
| 5 Tween 80 | 0.5 |
| 6 Polyethylene glycol 300 | to 100.0 |

*This product contains the equivalent of 25% v/v Absolute Alcohol.

The above example was prepared by mixing ingredients 1, 2, 4 and 5 in a vessel. Ingredient 3 was added with continuous stirring until dissolution was complete. The formulation was made up to volume with ingredient 6 and stirred. Examples 8–10 were prepared in a similar manner to Example 7.

| Sample Time | 30° C./60% Rh | 50° C. |
|---|---|---|
| 2 weeks | 49.7 | 49.4 |
| 1 month | 50.9 | 50.4 |
| 3 months | 50.7 | — |
| 6 months | 50.3 | — |

EXAMPLE 8

|  | % w/v |
|---|---|
| 1 Zotepine | 5.0 |
| 2 Lactic acid | 4.5 |
| 3 Ethanol 96%* | 26.0% v/v |
| 4 Flavour | 1.0% v/v |
| 5 Tween 80 | 0.5 |
| 6 Polyethylene glycol 300 | to 100.0 |

*This product contains the equivalent of 25% v/v Absolute Alcohol.

| Sample Time | 30° C./60% Rh | 30° C. | 40° C. | 50° C. |
|---|---|---|---|---|
| 2 weeks | — | 50.0 | 49.0 | 48.2 |
| 3 weeks | — | 51.4 | 50.1 | 48.7 |
| 4 weeks | 50.8 | 50.3 | 49.7 | 47.9 |

-continued

| | | |
|---|---|---|
| 3 months | 50.1 | — — — |
| 6 months | 50.2 | — — — |

EXAMPLE 9

| | % w/v |
|---|---|
| 1 Zotepine | 5.0 |
| 2 Citric acid | 4.5 |
| 3 Ethanol 96%* | 26.0% v/v |
| 4 Polyethylene glycol 300 | to 100.0 |

*This product contains the equivalent of 25% v/v Absolute Alcohol.

| Sample Time | 30° C. | 40° C. | 50° C. |
|---|---|---|---|
| 2 weeks | 50.0 | 49.6 | 48.2 |
| 3 weeks | 50.2 | 49.5 | 48.2 |
| 4 weeks | 50.5 | 48.4 | 47.9 |

EXAMPLE 10

| | % w/v |
|---|---|
| 1 Zotepine | 5.0 |
| 2 Malic acid | 4.5 |
| 3 Ethanol 96%* | 26.0% v/v |
| 4 Polyethylene glycol 300 | to 100.0 |

*This product contains the equivalent of 25% v/v Absolute Alcohol.

| Sample Time | 30° C. | 40° C. | 50° C. |
|---|---|---|---|
| 2 weeks | 49.8 | 50.3 | 49.1 |
| 3 weeks | 50.1 | 49.9 | 50.3 |
| 4 weeks | 49.8 | 48.8 | 48.8 |

Examples 11–13 are prepared in a similar manner to Example 7.

EXAMPLE 11

| | % w/v |
|---|---|
| 1 Zotepine | 5.0 |
| 2 Malic acid | 3.0 |
| 3 Ethanol 96%* | 26.0% v/v |
| 4 Polyethylene glycol 300 | to 100.0 |

*This product contains the equivalent of 25% v/v Absolute Alcohol.

EXAMPLE 12

| | % w/v |
|---|---|
| 1 Zotepine | 5.0 |
| 2 Tartaric acid | 2.0 |
| 3 Ethanol 96%* | 26.0% v/v |
| 4 Flavour | 1.0% v/v |
| 5 Tween 80 | 0.5 |
| 6 Polyethylene glycol 300 | to 100.0 |

*This product contains the equivalent of 25% v/v Absolute Alcohol.

EXAMPLE 13

| | % w/v |
|---|---|
| 1 Zotepine | 5.0 |
| 2 Citric acid | 2.5 |
| 3 Ethanol 96%* | 26.0% v/v |
| 4 Flavour | 1.0% v/v |
| 5 Tween 80 | 0.5 |
| 6 Polyethylene glycol 300 | to 100.0 |

*This product contains the equivalent of 25% v/v Absolute Alcohol.

EXAMPLE 14

| | % w/v |
|---|---|
| 1 Zotepine | 5.0 |
| 2 Lactic acid | 4.5 |
| 3 Ethanol 96%* | 26.0% v/v |
| 4 Flavour* | 1.0% v/v |
| 5 Polysorbate 80 | 0.5 |
| 6 Polyethylene glycol 300 | to 100.0 |

EXAMPLE 15

| | % w/v |
|---|---|
| 1 Zotepine | 5.0 |
| 2 Lactic acid | 4.5 |
| 3 Ethanol 96%* | 26.0% v/v |
| 4 Flavour* | 1.0% v/v |
| 5 Sodium metabisulphite | 0.1 |
| 6 Polysorbate 80 | 0.5 |
| 7 Polyethylene glycol 300 | to 100.0 |

TABLE 1

Zotepine-N-Oxide levels (% by HPLC) in Example 14 and 15 after storage in amber glass screw-capped bottles;

| Weeks | Storage condition | Example 14 | Example 15 |
|---|---|---|---|
| 0 | — | <LOD | <LOD |
| 2 | 40° C./75% RH | 0.16 | <LOD |
| | 50° C. | 0.56 | <LOD |
| 4 | 40° C./75% RH | 0.15 | <LOD |
| | 50° C. | 1.36 | <LOD |
| 8 | 40° C./75% RH | 0.46 | <LOD |
| | 50° C. | 3.48 | 1.07 |
| 12 | 25° C./60% RH | 0.12 | <LOD |
| | 30° C./60% RH | 0.14 | <LOD |
| | 40° C./75% RH | 0.63 | 0.47 |

<LOD means less than limit of detection.

These results demonstrate that the addition of an antioxidant e.g. sodium metabisulphite is advantageous in the preparation of a commercial product with a suitable shelf-life.

COMPARATIVE EXAMPLES

Formulations which are identical to those disclosed herein except that the organic acid used was acetic add gave unsatisfactory stability results.

What is claimed is:

1. A liquid pharmaceutical formulation comprising
   a) 2 to 7% w/v of Zotepine
   b) 0.5 to 35% w/v of an organic acid selected from the group consisting of ascorbic acid, citric acid, fumaric acid, glutaric acid, lactic acid, malic acid, sorbic acid and tartaric acid
   c) 15 to 60% v/v of ethanol and
   d) a liquid diluent to 100%.

2. A formulation according to claim 1 in which the liquid diluent is water, polyethylene glycol or sesame oil.

3. A formulation according to claim 1 which comprises
   a) 4 to 6% w/v of Zotepine
   b) 2 to 15% w/v of an organic acid selected from the group consisting of ascorbic acid, citric acid, fumaric acid, glutaric acid, lactic acid, malic acid, sorbic acid and tartaric acid
   c) 20 to 30% v/v of ethanol and
   d) polyethylene glycol to 100%.

4. A formulation according to claim 1 in which the organic acid is selected from the group consisting of citric acid, malic acid and lactic acid.

5. A formulation according to claim 1 in which the amount of organic acid used is in the range of 3 to 7% w/v of the formulation.

6. A formulation according to claim 1 which comprises
   a) 4 to 6% w/v of Zotepine
   b) 15 to 35% w/v of an organic acid selected from the group consisting of ascorbic acid, citric acid, fumaric acid, glutaric acid, lactic acid, malic acid, sorbic acid and tartaric acid
   c) 20 to 50% v/v of ethanol and
   d) water to 100%.

7. A formulation according to claim 6 in which the organic acid is selected from the group consisting of citric acid, malic acid and lactic acid.

8. A formulation according to claim 6 in which the amount of organic acid used is in the range of 18 to 32%, w/v of the formulation.

9. A formulation according to claim 6 in which the pH of the final formulation lies in the range of 2.2 to 2.6.

10. A formulation according to any previous claim in which the organic acid is lactic acid.

11. A formulation according to claim 1 which further comprises a preservative.

12. A formulation according to claim 11 in which the preservative is benzyl alcohol or an anti-oxidant or an anti-oxidant synergist or mixtures thereof.

13. A formulation according to claim 12 in which the anti-oxidant is selected from oneor more of the following: alpha tocopherol, ascorbic acid, ascorbyl palmitate, butylated hydroxyanisole, butylated hydroxytoluene, fumaric acid, malic acid, propyl gallate, sodium ascorbate and sodium metabisulphite and the anti-oxidant synergist is disodium edetate.

14. A liquid pharmaceutical formulation according to claim 1 comprising
   a) 2 to 7% w/v of Zotepine
   b) 2 to 15% w/v of an organic acid selected from the group consisting of ascorbic acid, citric acid, fumaric acid, glutaric acid, lactic acid, malic acid, sorbic acid, tartaric acid
   c) 20 to 30% w/v of ethanol
   d) 0.01 to 1.0% w/v of an anti-oxidant and
   e) polyethylene glycol to 100%.

15. A formulation according to claim 14 wherein the formulation comprises 4 to 6% w/v of zotepine.

16. A formulation according to claim 14 wherein the organic acid is selected from the group consisting of citric acid, malic acid and lactic acid.

17. A formulation according to claim 16 wherein the organic acid is lactic acid.

18. A formulation according to claim 14 wherein the amount of organic acid used is in the range of 3 to 7% w/v of the formulation.

19. A formulation according to claim 14 wherein the anti-oxidant is sodium metabisulphite.

20. A formulation according to claim 14 wherein the sodium metabisulphite is in the range 0.075 to 0.2% w/v.

21. A formulation according to claim 1 which further comprises one or more flavouring agents and/or one or more sweetening agents.

22. A formulation according to claim 1 which further comprises a surfactant.

23. A formulation according to claim 1 wherein the formulation shows a reduction of Zotepine content of less than 10% of the original Zotepine content by weight on storage at ambient temperature for 2 years.

* * * * *

UNITED STATES PATENT AND TRADEMARK OFFICE
CERTIFICATE OF CORRECTION

PATENT NO. : 6,239,165 B1
DATED : May 29, 2001
INVENTOR(S) : Dyer et al.

Page 1 of 1

It is certified that error appears in the above-identified patent and that said Letters Patent is hereby corrected as shown below:

Column 9, claim 10,
Line 49, "any previous claim" should be -- claim 1 --.

Column 10, claim 13,
Line 7, "oneor" should be -- one or --.

Signed and Sealed this

Sixteenth Day of October, 2001

Attest:

NICHOLAS P. GODICI
Attesting Officer
Acting Director of the United States Patent and Trademark Office